United States Patent [19]

Hamid et al.

[11] Patent Number: 4,494,835
[45] Date of Patent: Jan. 22, 1985

[54] POLYCONDUCTOR DEVICE FOR LASER BEAM DETECTION AND PROTECTION

[75] Inventors: Michael Hamid, Winnipeg, Canada; Anastasios Lionis, Vlissingen, Netherlands

[73] Assignee: The United States of America as represented by the Secretary of the Navy, Washington, D.C.

[21] Appl. No.: 403,596

[22] Filed: Jul. 30, 1982

[51] Int. Cl.³ .......................... G02C 1/00; G01J 1/42
[52] U.S. Cl. ..................................... 351/158; 356/218
[58] Field of Search ............... 356/218, 226; 351/158; 250/370 L

[56] References Cited

U.S. PATENT DOCUMENTS 3,597,054  8/1971  Winter ................................. 351/158

Primary Examiner—Rodney B. Bovernick
Attorney, Agent, or Firm—R. F. Beers; C. D. B. Curry; G. L. Craig

[57] ABSTRACT

A device is described using at least one polyconductor film as an active element lens of an electrical circuit for detecting incident laser radiation. In several alternative embodiments, a polyconductor film is located at the focal point of at least one lens which focuses the incident laser radiation on the film. The polyconducting film acts as a variable resistor of a balanced bridge network and upon receipt of radiation causes an imbalance in the bridge for radiation detection. The film changes phase with increasing incident power such that it protects itself against high levels of radiation. The lenses can also be polyconducting films and another film shielded from the radiation may be included to compensate for temperature fluctuations and maintain circuit sensitivity.

6 Claims, 8 Drawing Figures

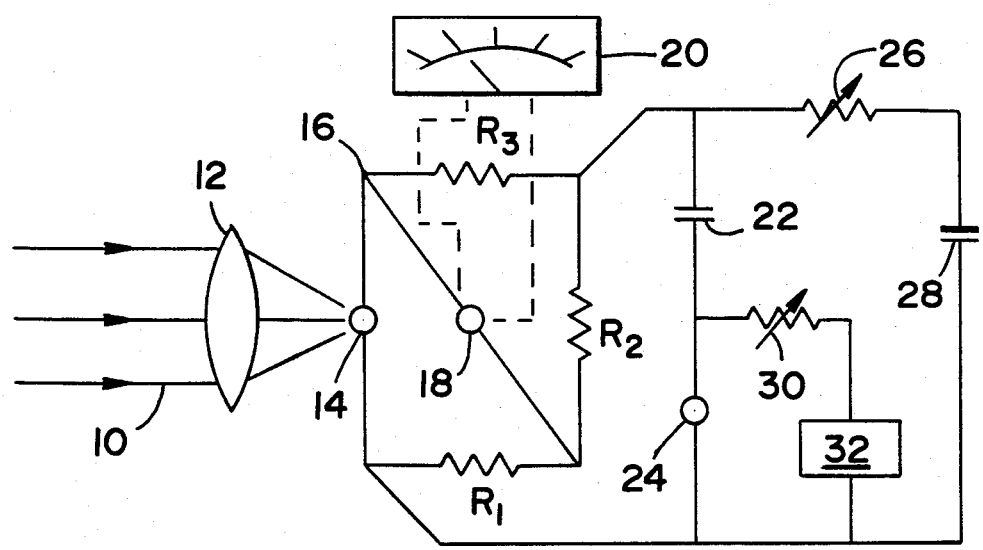
FIG _ 1
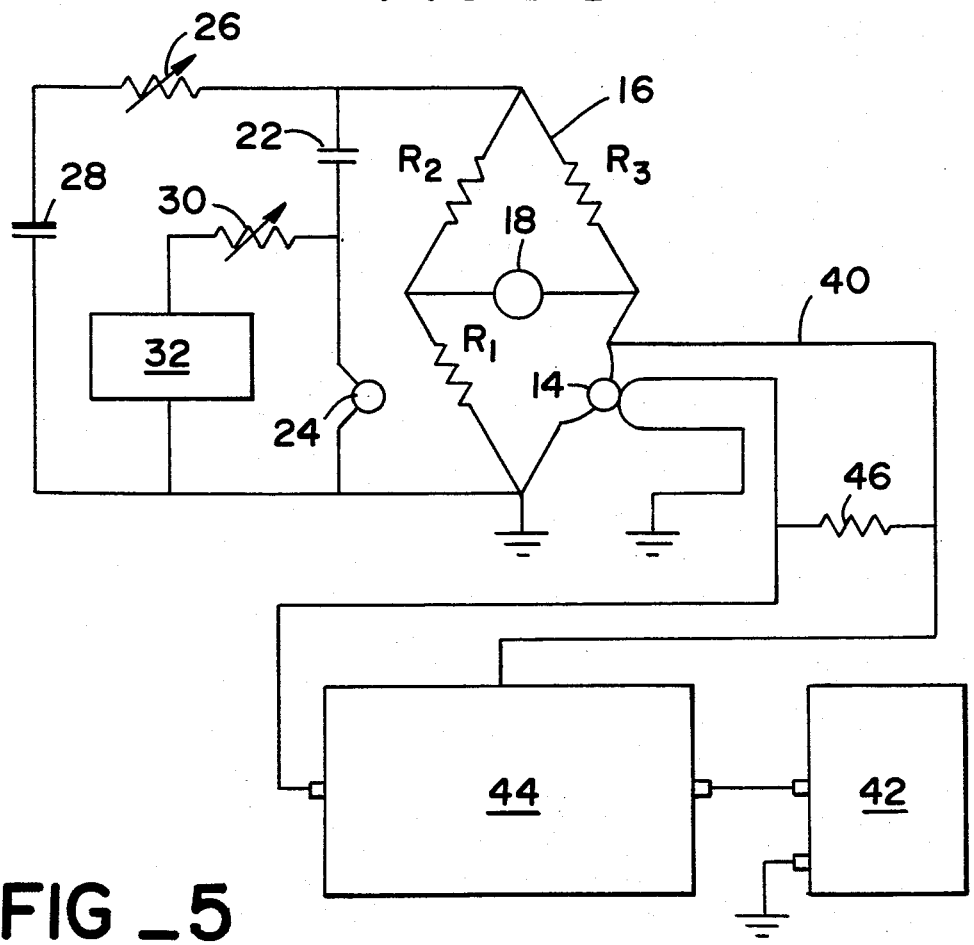
FIG _ 5

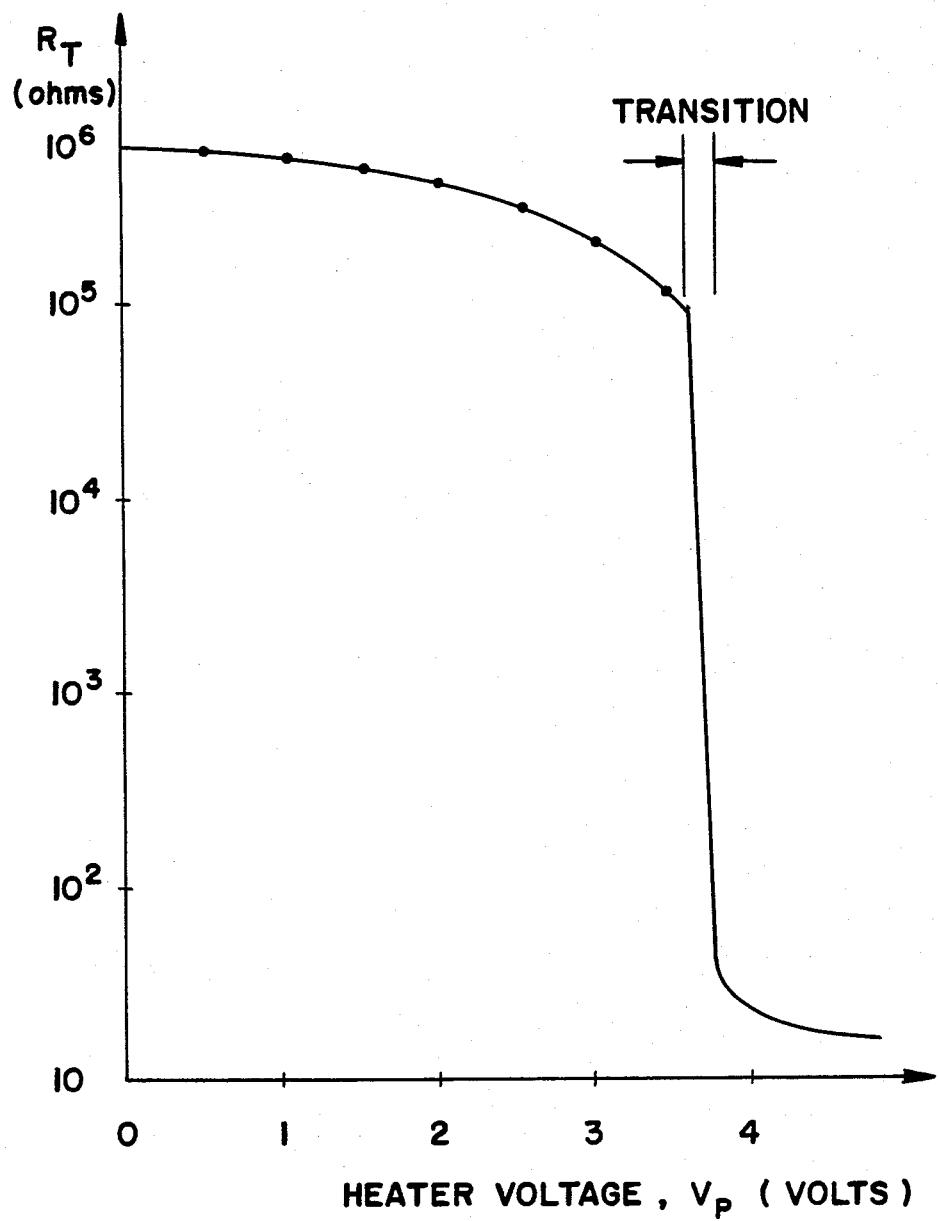
FIG_2

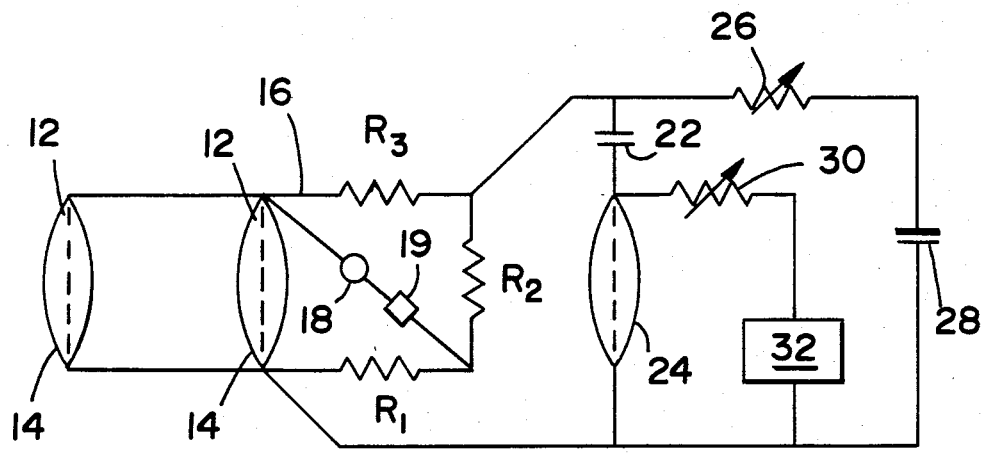
FIG _3 A
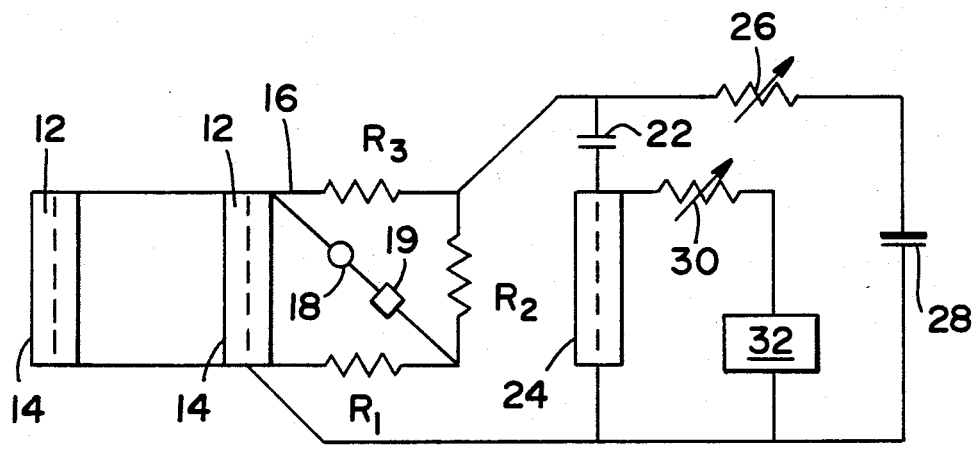
FIG _3 B

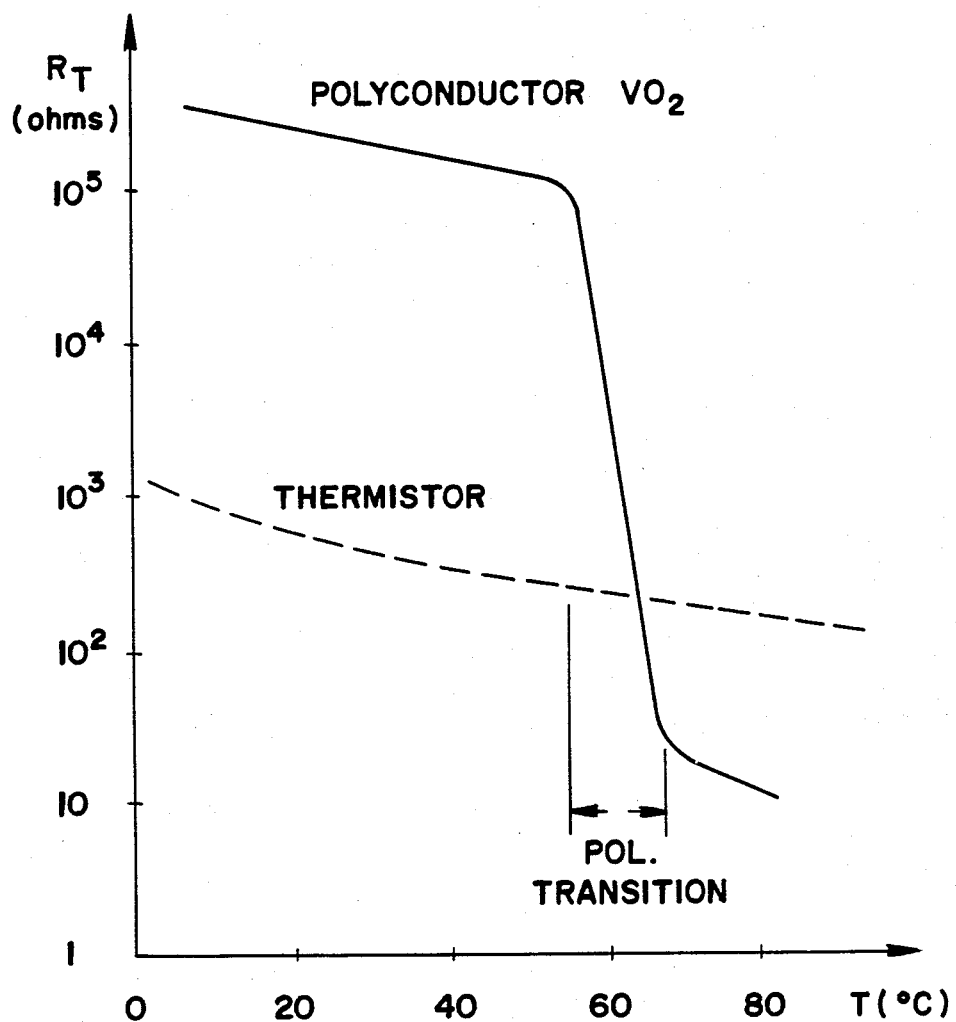
FIG_4

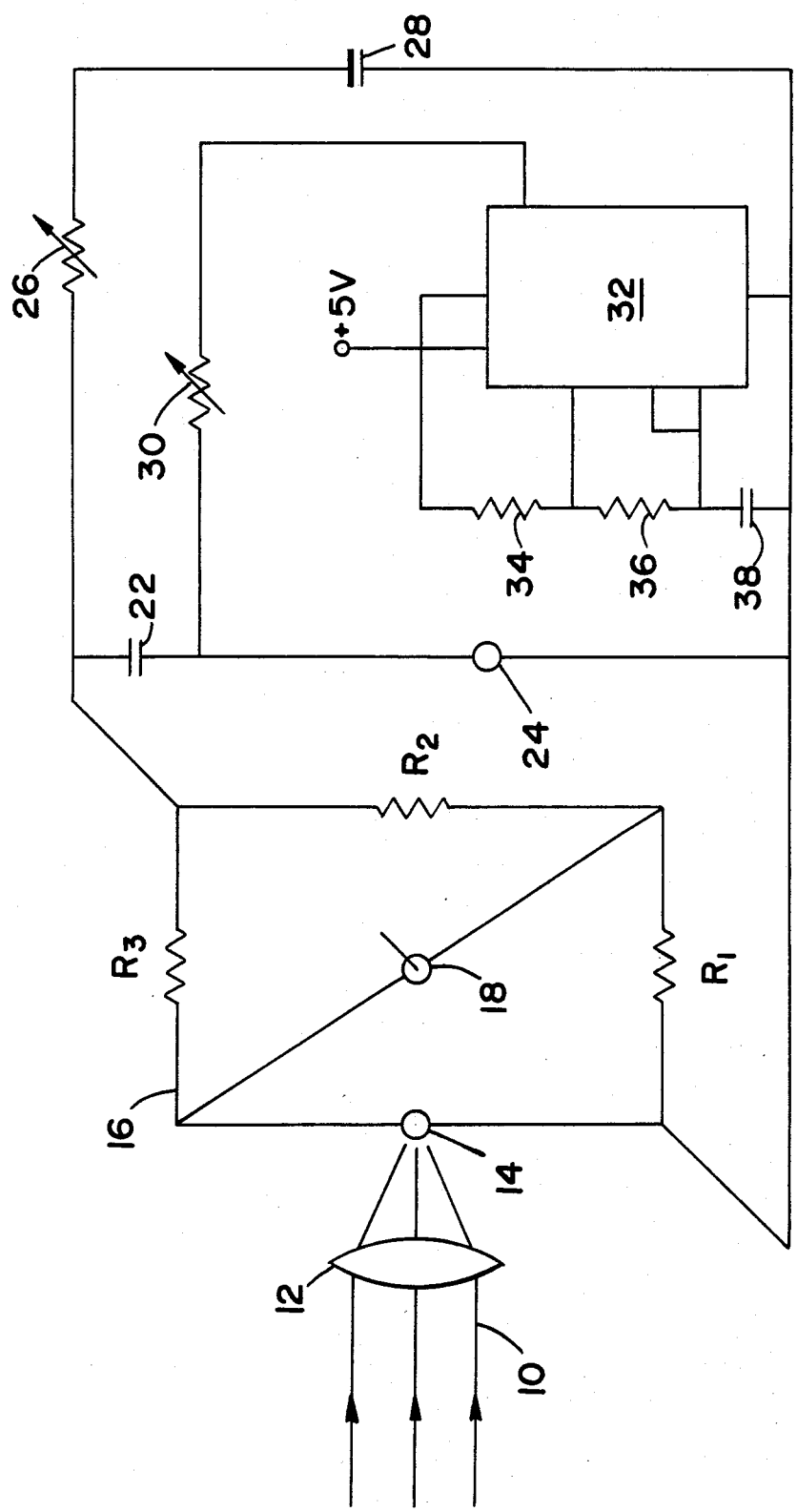
FIG_6

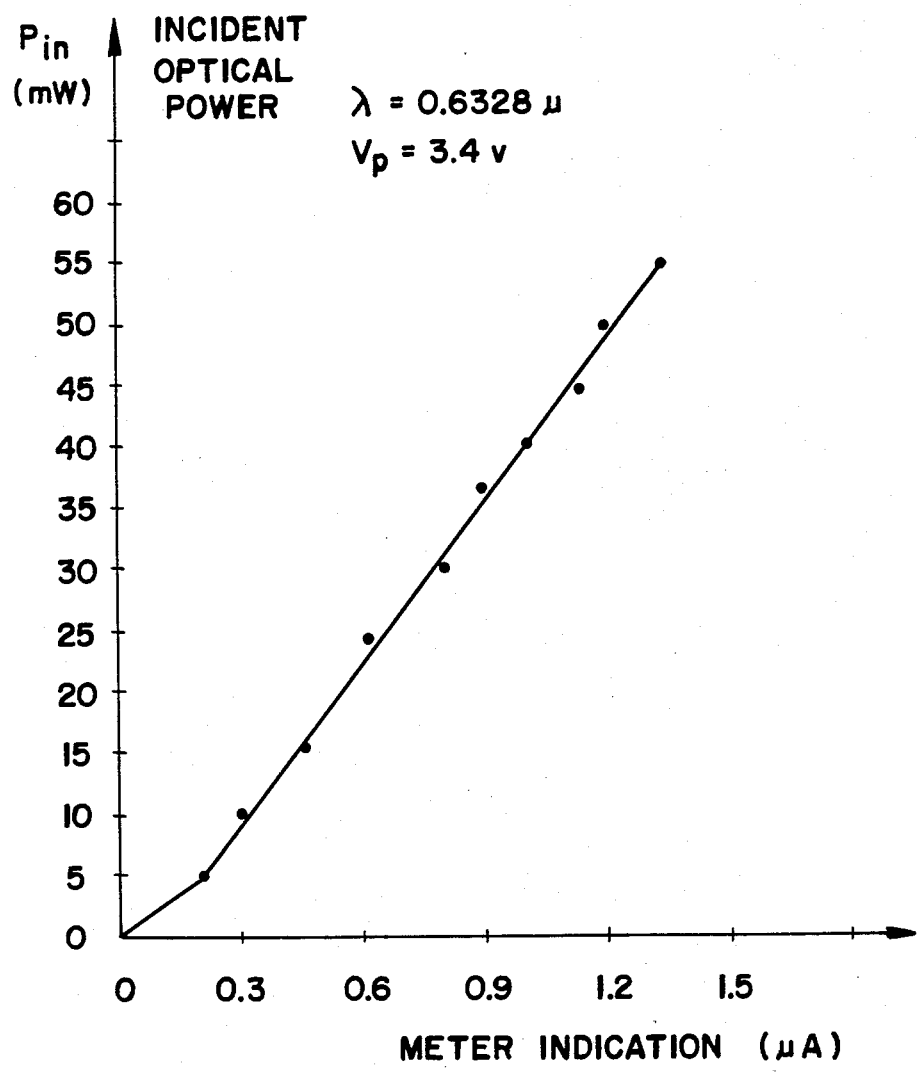
FIG_7

POLYCONDUCTOR DEVICE FOR LASER BEAM DETECTION AND PROTECTION

BACKGROUND OF THE INVENTION

1. Field of the Invention

The invention relates to a device for detecting incident laser radiation and determining the intensity of the radiation. More particularly, the present invention relates to a device using polyconducting film to detect incident laser radiation, to compensate for ambient temperature fluctuations, and to provide self-protection against high intensity radiation by changing phase dependent upon the incident radiation intensity level.

2. Description of Prior Art

Optical radiation detectors may be broadly divided into two main categories: thermal detectors and photon detectors. Photon detectors are more sensitive and include photomultipliers, photoconductors, photodiodes and avalanche photodiodes. Thermal detectors are less common but have the advantage of larger bandwidth and do not require cooling. Such detectors are effective for detection but have a response time too slow to provide effective or self-protection when exposed to high intensity laser beams.

Thermal detectors operate on the principle that the heating effect of the incident radiation causes a change in some electrical property of the detector, e.g. resistance, and thus the theoretical response is proportional to the energy absorbed and is practically the same over a wide range of the wavelength, especially in the infrared portion of the spectrum. The time constant is generally a few milliseconds and hence these detectors are rarely used where fast response times and high data rates are required.

Photon detectors operate on the principle that there is a direct interaction between the incident photons and the electrons of the detector material and thus that the detector response is proportional to the number of photons absorbed. These detectors usually have sensitivity one or two orders of magnitude greater than thermal detectors and time constants of generally a few microseconds. However, their spectral response varies with wavelength and the majority require cooling. The present invention is a device for detecting laser radiation and measuring laser power that is applicable to a wide variety of lasers and has very short response times permitting real-time detection and self-protection against heat degradation by high intensity lasers not possible by conventional thermal detectors.

SUMMARY OF THE INVENTION

The present invention is briefly described as a device for detecting and protecting against incident laser radiation by using at least one polyconductor film as an active element in an electrical network for detecting such radiation. The polyconductor film is located at the focal point of a lens, which may also be a polyconducting film, used to focus incident radiation on the film used as a variable resistor in a balanced bridge network. Receipt of radiation by the film causes an imbalance in the bridge producing an electrical signal whereby monitoring of the incident radiation and its intensity is possible. The polyconductor film changes phase with increasing incident power to provide self-protection against heat degradation.

BRIEF DESCRIPTION OF THE DRAWINGS

FIG. 1 schematically illustrates a first embodiment of a polyconductor device used to detect incident laser radiation.

FIG. 2 illustrates a typical terminal characteristic (terminal resistance v. heater voltage) of a polyconductor device as used in the instant invention.

FIGS. 3A, 3B schematically illustrate alternate embodiments of polyconductor devices used to detect and protect against incident laser radiation.

FIG. 4 illustrates comparative terminal characteristics (terminal resistance v. temperature) of a polyconductor device of the instant application and a conventional thermistor.

FIG. 5 schematically illustrates the instant invention compensated for ambient temperature fluctuations.

FIG. 6 schematically illustrates the instant invention modified for detection/protection against high-power laser radiation.

FIG. 7 illustrates a typical calibration curve of incident optical power v. meter indication for the instant invention.

DESCRIPTION OF THE PREFERRED EMBODIMENT

Referring to FIG. 1, a first embodiment of the instant invention is shown in which it is used as a detector of incident laser radiation. The incident laser beam 10 is focused by a lens 12 onto the polyconductor film 14 which constitutes one arm of a Wheatstone bridge circuit 16 having resistors $R_1$, $R_2$, $R_3$ in the other arms as shown. An indicating meter 18 may be placed in the center arm of the bridge and connected to a display 20 to monitor the incident power level. An external voltage source, not shown, supplies a bias voltage $V_P$ to the sensing polyconductor film 14. To compensate for ambient temperature fluctuations affecting sensor readings, a capacitor 22 and compensating polyconductor film 24 are connected in parallel with the bridge circuit 16 and a variable resistor 26 and bias voltage source $V_B$ 28 for the bridge. The compensating polyconductor film 24 is shielded from incident radiation. By way of example and not limitation, a typical film is type TC-1F-5V made by Multi-State Devices.

In the absence of an incident beam 10, the bridge 16 is balanced and the display meter 20 will indicate a zero power density level. In the presence of an incident beam, a voltage imbalance in the bridge 16 will develop due to a change in the bias voltage $V_P$ across the sensing polyconductor film 14. This imbalance will be shown on the display 20 which is calibrated with a standard optical power meter such that the intensity of the incident beam is directly read from the display. Compensation for temperature fluctuation is achieved by connecting the compensating polyconductor film 24 in parallel with a variable resistor 30 in series with an audio frequency (A.F.) supply 32. The terminal resistance of the compensating polyconductor film 24 increases as the temperature decreases resulting in more power being fed from the A.F. supply 32 to the bridge 16 as ambient temperature decreases. A typical terminal characteristic of this device (terminal resistance v. heater voltage) is presented in FIG. 2.

Thus, in operation, the bridge 16 is initially balanced with just direct current (D.C.) power from the bridge bias voltage source $V_B$ 28. The bridge bias voltage $V_B$ and the detector polyconductor bias voltage $V_P$ combine to drive the detector polyconductor to a terminal resistance of predetermined value corresponding to a sensitive quiescent point on its temperature-resistance curve.

Both bias voltages, $V_B$ and $V_P$ are selected to keep the bridge 16 balanced at the highest expected ambient temperature. For perfect zero-drift compensation, the increase in A.F. power from the A.F. supply 32 is just sufficient to keep the bridge 16 balanced. For greater sensitivity of the apparatus, the D.C. battery voltage $V_B$ may be replaced by an A.F. voltage. In this case, the bridge output could be amplified by a high gain amplifier having an output proportional to the optical power density of the incident beam.

A planar array or cluster of polyconductor films 14 whose center is approximately at the focal point of the lens 12 may be substituted for the single film and would have the advantage over a single film of less uncertainty concerning the exact location of the focal point of the lens 12 and greater capability to detect beams incident from different angles (other than normal incidence). In this case total power rather than power density would be detected by the array if a sufficiently large array is used.

Referring to FIG. 3A, an alternative embodiment is schematically shown as a circuit to be incorporated into a pair of eyeglasses for eyesight protection. Two lenses 12, each having a thin sensing polyconductor film 14 across the exterior surface are parallel connected to the Wheatstone bridge 16 as shown. An audio alarm 19 may also be connected in series with or in place of the indicating meter 18. Whichever film is exposed to the incident radiation would cause an approximate open circuit terminal resistance of the other parallel-connected film (due to the small cross-section of the incident beam). Again the bridge 16 would be imbalanced and the audio alarm 19 would activate.

Referring to FIG. 3B, a third embodiment of the instant invention is schematically shown. The circuit may employ a number of flat transparent surfaces 12 having the polyconductor film 14 on the exterior surface, the surfaces all connected in parallel to form one arm of the bridge 16. Thus for example protection against stray laser radiation may be provided in laboratories having viewing windows.

In all embodiments of the instant invention, the reflectivity of the polyconductor film 14 increases with increasing intensity of the incident beam until the film 14 changes state from a semiconductor to a metal. Thus the instant eyesight protection apparatus is self-protecting against thermal degradation as well as providing eyesight protection against intense laser radiation. These advantages are evident from FIG. 4 which shows a typical terminal characteristic (terminal resistance v. temperature) of a vanadium dioxide ($VO_2$) polyconductor device employed in this invention as compared to that of a typical thermistor device presently used in commercial thermal detectors.

Referring to FIG. 5, by way of example and not limitation a schematic of the preferred embodiment is shown having specific components permitting incident radiation detection with greater sensitivity than a thermistor detecting element. Here $R_1$, $R_2$, $R_3$ of the bridge 16 are 1k$\Omega$. The A.F. power supply 32 is a SIGNETICS 555 Timer having a +5 V applied bias voltage and two 1k$\Omega$ resistors 34, 36 and a 0.5 $\mu$f capacitor 38 connected to the output terminals of the timer. The timer 32 operates at 1000 Hz and the bridge bias voltage source $V_B$ is 3.5 V. The capacitor 22 is 1 $\mu$f and the two variable resistors 26, 30 are used to precisely balance the bridge 16.

In order to protect against high incident power levels such as might be found in military applications which vary over a large dynamic range, a modification of the proposed bridge circuitry is necessary. This is in order to keep the operating point of the bridge 16 in the same region of the terminal characteristic of the detecting film 14. The modification is required for large incident power levels which have the tendency of moving the operating point excessively far from the starting region. In addition to preserving the sensitivity of the polyconductor film 14 which is maximum in the transition region, it is also desirable to preserve the sensitivity of the bridge 16 by keeping the terminal characteristic $R_T$ reasonably low and selecting the resistors $R_1$, $R_2$, $R_3$ in the other three arms of the bridge close to the value of $R_T$. In addition, for metering purposes it is desirable to keep the current through the film 14 from all sources and hence the surface impedance of the film constant so that the scattering pattern and cross section will also remain constant. To achieve these objectives, a feedback loop is introduced in order to adjust the independent bias voltage $V_P$ of the sensing polyconductor as shown in FIG. 6. The feedback circuit 40, consists of a power supply 42 connected to a voltage regulator 44 which has a resistor 46 connected across the output terminals and is connected to the sensing polyconductor film 14.

In principle, an increase in the incident power level leads to a decrease in $R_T$ and thus moves the operating point away from the quiescent point. The proposed feedback loop senses this tendency and is immediately activated such that the bias voltage $V_P$ is decreased proportionately in order to restore operation at the quiescent point. In other words the loop serves the purpose of trading off $V_P$ with $R_T$ in order to produce bias control. Since the real time variations of $V_P$ could also be produced by ambient temperature fluctuations through changes in $R_T$, the proposed loop serves the purpose of protecting the sensing device (by decreasing the bias voltage) not only from high incident power levels but also from large sudden changes in ambient temperature. Such conditions are frequently encountered in electronic warfare applications and the proposed loop would provide such protection for the polyconductor device as well as any object coated with polyconductor films. If the temperature compensating polyconductor 24 is also protected from large temperature variations by a similar loop, not shown, (which will restore operation to the starting bias region) then the variations in its bias voltage $V_P$ (corresponding to $R_P$) can be monitored and used to calibrate a digital thermometer (or a profile thermometer if several temperature compensating polyconductors are used). With the operation of both loops it is possible to distinguish between large variations in incident power as opposed to large variations in ambient temperature and hence provide information for eliminating many types of false alarms in situations in which high incident power levels occur. It should also be noted that in the presence of both loops the sensing polyconductor becomes double compensated for ambient temperature variations since the current in the detecting film 14 is compensated by the compensating polyconductor 24 (through the Wheatstone bridge 16) while the heater bias voltage is compensated by the feedback loop 40. As a result of this double temperature compensation the bridge output meter 18 has a more stable indication. This is illustrated in FIG. 7 for a helium-neon laser of 60 mw output power and operating at a wavelength of $0.6328\mu$ or $0.6328 \times 10^{-6}$ meters.

What is claimed is:

1. An apparatus for detecting and protecting against high intensity laser radiation comprising:
   (a) a lens to focus said laser radiation at a predetermined spot;
   (b) at least one radiation sensing polyconducting film positioned approximate said predetermined spot, said film having points for electrical connection such that a film bias voltage may be applied across said film and such that said film may be operably connected in an electrical network;
   (c) a Wheatstone bridge circuit comprising a portion of said network in which said polyconducting film constitutes one arm of said bridge circuit to a predetermined voltage level;
   (d) means for electrically compensating voltage variations in said bridge network induced by ambient temperature fluctuations; and
   (e) means for reading voltage variations in said bridge network from said predetermined voltage level.

2. An apparatus as recited in claim 1 wherein said bias voltage is obtained via a direct current voltage source series connected to a variable resistor and operably connected across said bridge network.

3. An apparatus as recited in claim 1 wherein said compensating means additionally comprises:
   (a) a compensating polyconductor film operably parallel connected to a series-connected variable resistor and audio frequency power source, the combination of said film, said resistor and said power source being series-connected to a capacitor and the result operably connected across said bridge circuit.

4. An apparatus as recited in claim 1 wherein said reading means is a galvanometer sensing changes in voltage across said bridge and outputting a corresponding signal to a display.

5. An eyesight protection apparatus for protecting against high intensity laser radiation comprising:
   (a) a conventional pair of eyeglass frames having a right and a left lens;
   (b) a first thin radiation sensing polyconductor film overlaying the exterior of said right lens, said first thin film being transparent and having four electrical contact points such that it may be incorporated into an electrical circuit;
   (c) a second thin radiation sensing polyconductor film overlaying the exterior of said left lens, said second thin film being transparent and having four electrical contact points such that it may be incorporated into an electrical circuit;
   (d) a Wheatstone bridge electrical circuit, said first thin film and said second thin film parallel connected to form one resistance arm of said bridge circuit;
   (e) a film bias voltage source operably connected to said first and said second thin films to maintain a predetermined voltage across said films;
   (f) a compensating circuit operably connected across said bridge circuit to compensate for ambient temperature fluctuations affecting said circuit; and
   (g) an alarm operably connected to the middle arm of said bridge circuit, said alarm being activated upon sensing a voltage imbalance in said bridge.

6. The apparatus of claim 5 wherein said film bias voltage source is an electrical feedback circuit further comprising:
   (a) a power supply having an output; and
   (b) a voltage regulator receiving the output of said power supply and operably connected across said radiation sensing polyconducting film(s) to provide a feedback bias voltage.

* * * * *